(12) United States Patent
Sánchez Álvarez et al.

(10) Patent No.: US 12,156,660 B2
(45) Date of Patent: Dec. 3, 2024

(54) INSTRUMENTAL ALIGNMENT SYSTEM USED IN TOTAL KNEE ARTHROPLASTY

(71) Applicants: SANTXARIZMENDI GRUPO DE INVESTIGACIÓN S.L, Vitoria-Gasteiz (ES); MIZAR ADDITIVE MANUFACTURING S.L.U., Vitoria- Gasteiz (ES)

(72) Inventors: José Miguel Sánchez Álvarez, Vitoria-Gasteiz (ES); Xabier Sánchez Arizmendiarrieta, Vitoria-Gasteiz (ES); Gorka Fernández Alzola, Miñano (ES); Ainhoa Lete Lezeta, Miñano (ES)

(73) Assignees: SANTXARIZMENDI GRUPO DE INVESTIGACIÓN S.L, Vitoria-Gasteiz (ES); MIZAR ADDITIVE MANUFACTURING S.L.U., Vitoria-Gasteiz (ES)

( * ) Notice: Subject to any disclaimer, the term of this patent is extended or adjusted under 35 U.S.C. 154(b) by 431 days.

(21) Appl. No.: 17/616,731

(22) PCT Filed: Jun. 2, 2020

(86) PCT No.: PCT/ES2020/070365
§ 371 (c)(1),
(2) Date: Dec. 6, 2021

(87) PCT Pub. No.: WO2020/245483
PCT Pub. Date: Dec. 10, 2020

(65) Prior Publication Data
US 2022/0313286 A1    Oct. 6, 2022

(30) Foreign Application Priority Data

Jun. 6, 2019 (ES) ............................... ES201930512

(51) Int. Cl.
*A61B 17/17* (2006.01)
*A61B 17/15* (2006.01)
(Continued)

(52) U.S. Cl.
CPC ........ *A61B 17/1764* (2013.01); *A61B 17/155* (2013.01); *A61B 17/1675* (2013.01); *A61F 2/3859* (2013.01); *A61B 2034/108* (2016.02)

(58) Field of Classification Search
CPC .............. A61B 17/1764; A61B 17/155; A61B 17/1675; A61B 2034/108; A61F 2/3859
See application file for complete search history.

(56) References Cited

U.S. PATENT DOCUMENTS

2017/0071677 A1* 3/2017 Utz ........................ A61B 34/20
2019/0274696 A1* 9/2019 Goble .................. A61B 17/155

FOREIGN PATENT DOCUMENTS

EP          3095398 A1    11/2016
WO    2012/176077 A1    12/2012

OTHER PUBLICATIONS

Sanz-Ruiz P et al., "Individualized Moulds for Alignment of Primary Knee Arthroplasty", Acta Ortopédica Mexicana, pp. 100-105, (2014).

* cited by examiner

*Primary Examiner* — Sameh R Boles
(74) *Attorney, Agent, or Firm* — FISHERBROYLES, LLP; Roger L. Browdy; Ronni S. Jillions

(57) ABSTRACT

A customized alignment system of the instruments used in total knee arthroplasty. The alignment system includes a fixed femoral guide and a tibial guide configured to adapt to the femur and the tibia, resting on these bones without invading the cartilage of the articular surfaces. The tibial guide and two joinable femoral guides that can be coupled to the fixed femoral guide allow performing bone perfora- (Continued)

tions adequately arranged to allow subsequent placement of cutting guides for the placement of a conventional total knee prosthesis. The guides are designed from a preoperative bone model. The system provides a more precise alignment compared to other conventional techniques, avoids the use of intramedullary alignment and simplifies surgery for the placement of a total knee prosthesis.

22 Claims, 17 Drawing Sheets

(51) Int. Cl.
     *A61B 17/16*     (2006.01)
     *A61F 2/38*     (2006.01)
     *A61B 34/10*     (2016.01)

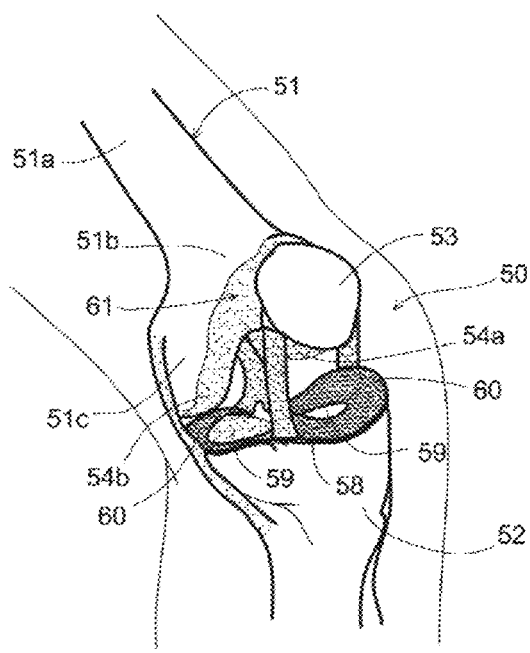
FIG.1
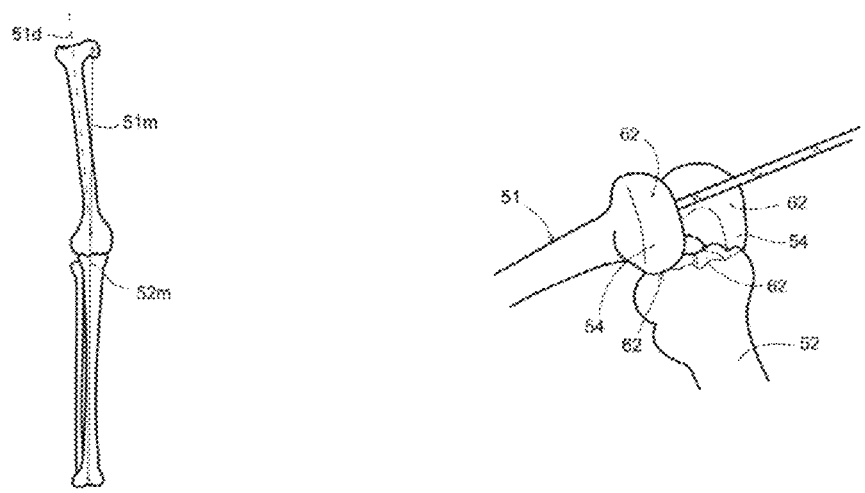
FIG.2
FIG.3

INSTRUMENTAL ALIGNMENT SYSTEM USED IN TOTAL KNEE ARTHROPLASTY

TECHNICAL FIELD

The invention relates to a system suitable for surgical use, in particular in total knee arthroplasty procedures. It is a system for the alignment of conventional cutting instruments usually used to perform bone resections necessary for the subsequent placement of a knee prosthesis. The invention also relates to a method for designing such an alignment system.

STATE OF THE ART

The mobile joints, such as the knee, shoulder or hip, constitute junction points between bones allowing a series of relative mechanical movements between said bones. In particular, the knee joint serves as a link between the thigh and the leg connecting the femur to the tibia, enabling flexure and extension movements along with limited rotation in the flexure position. These movements are possible thanks to the joint action of the femur, the tibia, and a third bone, the patella, which acts as a pulley to allow flexure and extension movements. The articular cartilage, located at both ends of the femur and the tibia and on the inner side of the patella, covers the articular surfaces. The function of the articular cartilage is protecting the bones of the joint and taking part in the mechanics of movements, cushioning loads, and providing lubrication. As in other joints, a strong capsule placed around the joint strengthens the binding between the bones, providing joints strength and stability. Additionally, a number of ligaments strengthen the binding and restrict joint movements in certain directions.

Osteoarthritis is a common condition among different disorders affecting the knee joint. Osteoarthritis is a degenerative disease caused by a deterioration of articular cartilage as a result of aging or injury. When degeneration of joint cartilage occurs, it affects protection, and lubrication usually provided to joint surfaces. Consequently, friction occurs between the bone surfaces causing rigidity and pain. There is no cure for osteoarthritis, although there are conservative therapies aimed at alleviating associated symptoms and delaying degeneration. However, in cases of severe or advanced degeneration, the most appropriate indication is the implantation of a knee prosthesis to replace the damaged structures.

Partial prostheses are known, to be applied in cases in which joint disease only partially affects the joint. These prostheses are implanted through conservative surgery aimed at the dedicated replacement of the diseased area of the affected bone, which normally allows for a quick recovery. However, in many cases, full surgical replacement of the knee joint with a prosthesis is required to replace diseased joint surfaces. The object is to eliminate pain, restoring joint movement and function to the muscles, ligaments, and other soft tissues that control the joint. This surgical procedure is known as Artroplastia Total de Rodilla (ATR) or Total Knee Arthroplasty (TKA) in English.

For the implantation of a Total Knee Prosthesis (TKP) that restores the function of the joint, a resection of the diseased or arthritic areas of the femur, tibia, and patella it required. Subsequently, two or three prosthetic components are implanted: one in the tibia, another one in the femur, and, if necessary, a third patellar component. The materials used in total knee prostheses are designed to allow slightly lower mobility than that of the normal joint. Components are usually made up of a metallic member that fits exactly into a plastic member. Various metals, such as stainless steel, cobalt alloys, and chrome or titanium are used. Plastic is usually high-density polyethylene, extremely durable, and wear-resistant. Cement can be used to fix the components of the prosthesis to the bone. There are also uncemented prostheses embedded directly in the bone.

For implantation of a total knee prosthesis by TKA, specific instruments are used, consisting of alignment and guiding systems, so that the surgeon can perform the necessary cuts or resections in femur and tibia as accurately as possible, so that, subsequently, the prosthetic components on the resected bones can be placed. Alignment systems currently used involve making various incisions and perforations in the femur and tibia in order to place conventional cutting guides. Conventional cutting guides allow a first distal cut to be made successively in the femur, followed by four other cuts to shape the femur and another cut in the tibia. Prosthetic components are placed on the sectioned bones during surgical procedure. Before making resections, the cutting guides must be properly positioned and aligned, with the correct alignment of these cutting guides being considered one of the key factors for the success of a TKA.

Two types of systems are currently used to align the cutting guides. On one hand, intramedullary alignment systems (standard systems) use intramedullary (IM) references. These standard alignment systems are based on the use of intramedullary rods that cross the bone marrow canal and which can sometimes be associated with excessive bleeding.

Furthermore, customized alignment systems use extramedullary (EM) references. This type of system has undergone notable development in recent years, based on the design of specific instrumentation for each patient (specific cutting blocks), seeking a more precise positioning of the femoral and tibial prosthetic components in order to achieve greater success rate in the TKA, Patient-specific approaches rely on preoperative imaging of the knee, hip, and ankle to assess the overall limb alignment. The images can be obtained using known techniques, such as computed tomography (CT/ACT) or magnetic resonance imaging (MR/NMR), obtaining a three-dimensional model of the anatomy of the patients lower limb. From this three-dimensional model, the anatomical marks of the patients knee can be identified, generating 3D models of the femoral and tibial components of optimal size, position, and alignment. The procedure includes a preoperative plan for bone resections. From this preoperative study, the appropriate parameters of orientation, resection depth, location, and rotation are determined, and extramedullary customized blocks or cutting guides are manufactured for the alignment and placement of the prosthesis during the TKA. These customized guides or blocks do not require the introduction of instruments through the intramedullary canal.

In any case, TKA is a critical surgical procedure that requires great expertise on the part of the surgeon. Excessive bone resection or a slight misalignment can lead to joint instability or early loosening of the components. In short, excessive bleeding or insufficiently precise placement of the prosthetic components are factors that compromise the success of a TKA.

Various comparative studies have been published between conventional alignment systems and alignment systems based on specific cutting blocks. For example, the publication "Individualized Moulds for Alignment of Primary Knee Arthroplasty"; Sanz-Ruiz P, Matas-Diez J A, Pérez-Martin A, Vaquero-Martín J; Acta Ortopédica Mexicana, 2014. The publication proposes a comparative analysis between different specific cutting block systems (ECB), which use different imaging methods for the preoperative planning, this publication also comparing the results obtained to standard alignment systems. Theoretical advantages of the specific systems are pointed out, concerning the possibility of making a more precise a priori preoperative planning, reducing the surgical time and the necessary instruments and causing less bleeding by not crossing the intramedullary canal. Despite these theoretical advantages, the specific systems involve additional costs, not being exempt from possible errors in the design process. The publication is also inconclusive regarding the most suitable imaging technique.

In line with the above, further scientific works have questioned the advantages of customized extramedullary guides versus conventional intramedullary systems. Among the most recent, it is worth mentioning the publication "Patient Specific Instrumentation (PSI) in Total Knee Arthroplasty. Should we adopt it?"; Ana Sofia Teles Rodrigues, Manuel Antonio Pereira Gutierres; Universidad de Oporto, Facultad de Medicina, Departamento de Ortopedia y Traumatologia, 2016. In this publication, several of the previously set concepts are explained and a comparative study is carried out between standard instrumentation (Standard Instruments (SI)) and specific instrumentation for each patient (Patient Specific Instruments (PSI)), analysing alignment, costs, the effectiveness of the technique and the postoperative functional evaluation of each system. The paper starts by highlighting the significance of limb alignment after TKA, as component placement errors are associated with a lower function and compromised long-term performance. On the other hand, the publication anticipates an increase in the demand for the TKA technique in the future, due to demographic reasons and longevity. Therefore, the improvement of this surgical technique is considered very important. The publication highlights that misalignment of the tibial and femoral components remains a major concern, as deviations exceeding 3° of varus/valgus on the mechanical axis are currently associated with TKA failure. Consequently, the tibial and femoral components should be positioned as accurately as possible. Despite the potential surgical benefits of using patient-specific cutting blocks, It is considered that there are no conclusive Fangterm implant survival data to support its use. The advantages of these systems remain controversial. The paper explains that the precision of anatomical landmarks is crucial for the final precision of the technique. In the event of joint deformities, the accuracy of the preoperative images may be compromised. Finally, some studies consider that the precision obtained between TKAs performed with PSI and those performed with SI is comparatively similar. The paper's conclusion establishes that, based on the reviewed scientific work, both techniques are capable of restoring the alignment of the extremities and positioning the prosthetic components with equivalent precision. Therefore, the profitability or unquestionable benefits for TKA through PSI are not considered proven. Consequently, given the current demand and importance of TKAs and the high health budget involved, any improvement in the technique is considered of great importance and interest.

The aim of the invention is a system for the alignment of instruments used for bone resections in Total Knee Arthroplasty that improves the precision of known alignment systems and simplifies surgical procedure.

BRIEF DESCRIPTION OF THE INVENTION

It Is an object of the invention an improved system for customized extramedullary alignment of the instruments (cutting guides) commonly used in total knee arthroplasty. The alignment system of the invention is characterized in that it comprises a fixed femoral guide intended to be placed on the femur of a patient. The fixed femoral guide, which comprises a curved surface partially delimited by an irregular edge, is configured to fit and tightly contact the femur surrounding the articular surface of the femoral condyles but without overlapping said articular surface. The fixed femoral guide comprises a fixation element for allowing the fixed femoral guide being fixed to the femur. The fixed femoral guide also comprises a connection element through which two joinable femoral guides can be detachably and consecutively coupled. These joinable femoral guides allow for making femoral perforations compatible with the use of conventional femoral cutting guides, as will be detailed later herein. The alignment system of the invention also comprises a tibial guide intended to be placed on an anteromedial region of the patient's tibia, surrounding the articular surface of the tibia but without overlapping said articular surface.

Thanks to the structural configuration of the fixed femoral guide, it is possible to place or lean it on a healthy part of the femur, unlike other customized alignment systems that are placed on parts of the articular surfaces diseased or affected by osteophytes (pathological bone resulting from joint degeneration and cartilage defects difficult to segment). Consequently, a greater precision of the location of the perforations, on which the conventional cutting guides used for bone resections will subsequently be placed, is obtained. The tibial guide of the system of the invention also rests on healthy bone, as with the fixed femoral guide.

The alignment system of the invention is designed to be compatible with known conventional cutting guides, with the consequent economic advantages.

Furthermore, since it does not require intramedullary intervention, the alignment system of the invention implies a less invasive performance compared to conventional alignment systems of this type.

Another object of the present invention is a method for designing the alignment system. The design method comprises a previous step for obtaining a bone model of the patient's lower extremity, in order to carry out preoperative planning for the customized design of the guides. Preferably, the bone model is obtained from a CAT scan, other diagnostic methods that provide equivalent precision being admissible.

The use of the customized extramedullary alignment system of the invention eliminates the need to perform a series of operations, which are common during a conventional TKA, such as determining the size of the prosthetic component or the thickness of the tibial prosthetic component, which are calculated preoperatively from the bone model in the method of the invention.

In short, by using the alignment system of the present invention, better alignment is achieved, the placement of the prosthetic components is optimized, bleeding is reduced and surgical procedure is simplified.

It is not an object of the present invention the surgical procedure to carry out the implantation of the total knee prosthesis.

BRIEF DESCRIPTION OF DRAWINGS

The details of the invention are seen in the accompanying figures, which are not intended to limit the scope of the invention:

FIG. 1 shows a schematic view of the knee joint depicting some of the internal structures of its anatomy.

FIG. 2 shows a schematic representation of the femur and tibia, showing their mechanical and anatomical axes.

FIG. 3 illustrates some aspects of the conventional femoral alignment technique used in the Prior Art during a total knee arthroplasty.

DETAILED DESCRIPTION OF THE INVENTION

Figure 4A:
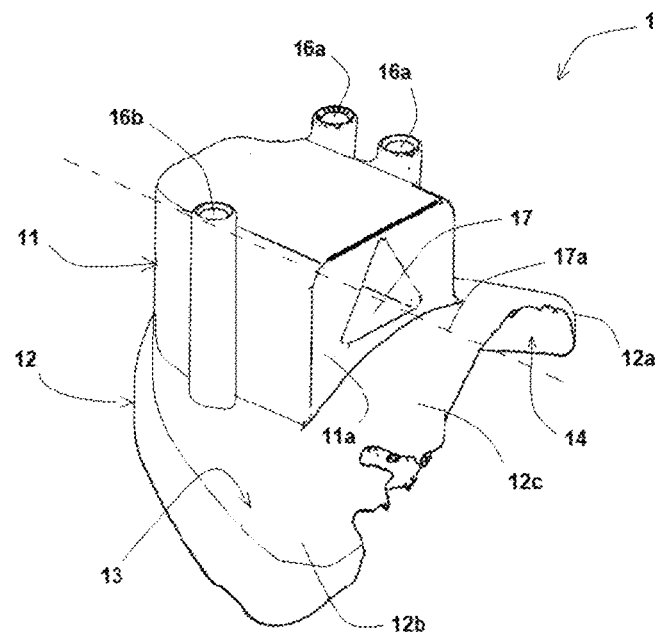
FIGS. 4A, 4B, 4C, and 4D show respectively a perspective, a top plan view, a rear view, and a bottom plan view of an embodiment of the fixed femoral guide of the alignment system according to the invention.

The system of the invention relates to an improved extramedullary alignment system for using in total knee arthroplasty and to a method of designing such a system.

Below is a review of some parts of the anatomy of the knee joint, as a preliminary step to understand the features and advantages of the invention that will be explained in detail later. FIG. 1 shows the anatomy of a knee joint (50) schematically depicting some of the internal structures of its anatomy. As can be seen in the drawing, the knee joint (50) binds the distal end of the femur (51) with the proximal end of the tibia (52), thus enabling the connection between the thigh and the leg and helping to support the body weight. The patella (53), articulated with the femur (51), allows flexure and extension movements. As in other long bones, an elongated core part or diaphysis (51a), located between two extremities or epiphysis (51c), can be distinguished in the femur (51). The joint is located in the epiphysis (51c) and the area in which the diaphysis (51a) binds to epiphysis (51c) is known as metaphysis (51b). The femur (51) comprises at its distal end two femoral condyles (54) or convexly rounded protuberances separated by an intermediate space called the intercondylar space. The anterior, inferior, and posterior aspects of the femoral condyles (54) are articular and define the femoral trochlea (56), provided with a central depression between the femoral condyles (54) by the anterior aspect of the femur (51). The femoral condyles (54) are not identical since the medial condyle (54b) protrudes more and is narrower than the lateral condyle (54a). Epicondyles are also present, which are bony elevations in the non-articular areas of the femoral condyles (54) and are bound by the epicondylar line. On the other hand, the proximal end of the tibia (52) comprises a tibial plateau (58) with two slightly concave glenoid cavities (59) intended to receive the femoral condyles (54). As in other mobile joints, two or more joint surfaces between which relative movement occurs are involved in the movement. The knee joint (50) is a complex joint, formed by two different joints: the main one, the femorotibial joint that connects the surfaces of the two femoral condyles (54) with the tibia (52), and the patellofemoral joint between the femoral trochlea (56) and the posterior part of the patella (53). The joint is enveloped by a fibrous joint capsule (not shown in FIG. 1) that constitutes a closed space that houses the patella (53), a portion of the distal end of the femur (51) and a portion of the proximal end of the tibia (52). Additionally, the joint action between the bones, femur (51), tibia (52), and patella (53) is complemented by the action of the menisci (60). The menisci (60) are two fibrocartilaginous structures arranged between the femur (51) and the tibia (52) on the tibial plateau (58), presenting a flatter lower face on the tibial plateau (58) and a more concave upper face that adapts to the femoral condyles (54). Its function is to improve the coupling between the articular surfaces, between the femoral condyles (54) and the glenoid cavities (59) of the patella (53), providing an elastic connection and participating in the transmission of compression forces between the femur (51) and the tibia (52). Thus, the menisci (60) distribute the forces in the knee and the loads that are exerted on the articular surfaces of the knee, reducing friction and contributing to the stabilization of the joint. The articular cartilage (61) covering the joint surfaces is arranged between the bones of the joint. Like other mobile joints, the bones are held together by the joint action of the joint capsule and the complementary work of a series of associated ligaments, intertwined with the capsular tissue. Ligaments strengthen the stability of the joint, allowing and facilitating limited knee joint movements and restricting other anatomically inappropriate or excessive movements. The above-detailed structures cooperate with the tendons, which are also part of the knee and whose function is to connect the bones to the muscles to transmit muscular force to the bone, making movement possible.

FIG. 2 schematically represents the mechanical and anatomical axes of the femur and tibia. The mechanical axis (51m, 52m) connects the centres of the hip, knee, and ankle joints. The anatomical or diaphyseal axis (51d) of the femur connects the centre of the intercondylar notch with the apex of the greater trochanter. As shown in figure, the mechanical (51m) and diaphyseal axis (51d) of the femur are not coincident, the diaphyseal axis (51d) forming an angle of about 170°-175° with the mechanical axis (52m) of the tibia.

In a healthy knee, the articular cartilage (61) that covers the articular surfaces of the femoral condyles (54), the tibial plateau (58), and the patella (53) are smooth and soft, allowing movements without pain. The deterioration of articular cartilage (61), as a result of injury or arthrosis or other diseases, can cause pain and functional limitation, causing a significant decrease in quality of life. Under this circumstance, the total replacement of the knee joint, which has suffered significant wear, with a prosthesis may be indicated.

The conventional TKA, known in the Prior Art, is a surgical technique performed under anaesthesia for a surgeon to replace the diseased joint with prosthetic components made of artificial materials. For this purpose, the distal end of the femur (51) is resected and the femoral condyles (54) are replaced by a first prosthetic component, usually made up with a metal, such as chromium, cobalt, or titanium. This first component is similar in shape to the femoral condyles (54). Additionally, the proximal end of the tibia (52) is resected for the subsequent placement of a second prosthetic component. On this second prosthetic component, shaped like a tray and provided with a normally metallic surface, some pieces of plastic (polyethylene) are placed to replace the menisci. Finally, if the replacement of the patella is necessary, a third plastic prosthetic component (polyethylene) will be placed, slidably with respect to the depression located between the two hemispheres of the first prosthetic component that replaces the femur, so that the patient perform knee flexure and extension movements without pain.

To perform the necessary osteotomies or resections in the knee bones, for the subsequent placement of the aforementioned prosthetic components, the alignment systems currently used allow conventional cutting guides to be placed to perform these resections as accurately as possible. The conventional protocol includes femoral intramedullary alignment, distal resection of the femur using a first block or cut guide, determination of femoral size, resections or anterior, posterior and oblique femoral bone osteotomies using a second cutting guide or cutting block 4 in 1, intramedullary or optionally extramedullary tibial alignment, tibial resection, determination of the tibial size, optional patellar resection and, finally, placement of the prosthetic components. FIG. 3 shows some aspects of the conventional femoral alignment technique for performing a TKA, using intramedullary alignment instruments. For this, a femoral alignment guide is usually used, which comprises a rod about 9 millimeters thick. This rod is inserted into the intramedullary canal of the femur until the guide for femoral alignment (not shown in FIG. 3) contacts the edge of the distal femoral condyle. Pins are placed on the femoral alignment guide on which the conventional cutting guide is mounted for distal resection of the femur. The complete conventional technique for performing the TKA is explained in various state of the art documents detailing the complete surgical protocol to follow.

The present invention provides an alternative alignment system that allows positioning the conventional cutting guides commonly used to perform the femoral and tibial resections, necessary for the placement of a TKP. The alignment system of the invention is designed from preoperative images of the patient's anatomy and is compatible with the use of conventional market cutting guides.

The invention also relates to a method for designing the alignment system. According to the method of the invention, preoperative planning of the patient's lower extremity is performed, obtained from a digital bone model. Based on this digital bone model, four specific alignment components or guides are designed for each patient: three alignment guides for the preparation of the femur and one alignment guide for the preparation of the tibia. Preferably, the bone model for the preoperative study is obtained from a CAT (Computed Axial Tomography), a technique deemed appropriate because it allows for a very precise reproduction of the anatomy of the femur and tibia in a suitable time. However, other diagnostic techniques that provide a precision similar to CAT scans, for example magnetic resonance or others, are deemed compatible with the invention.

Figure 4B:
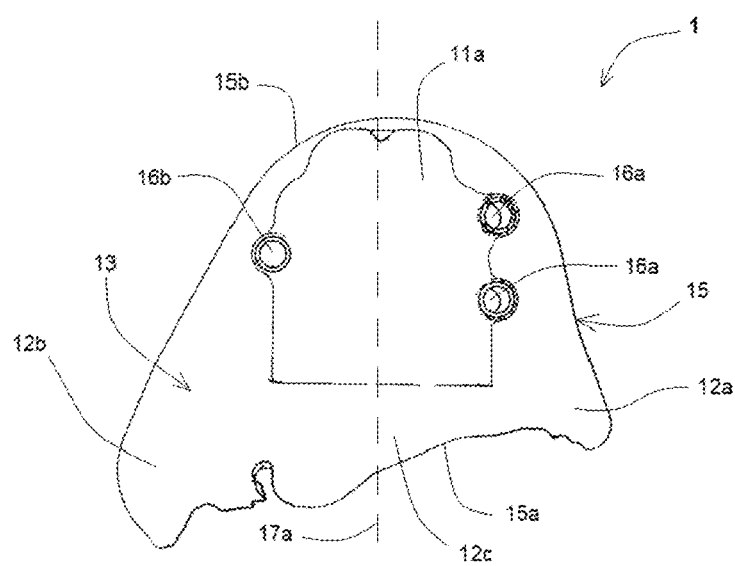
Figure 4C:
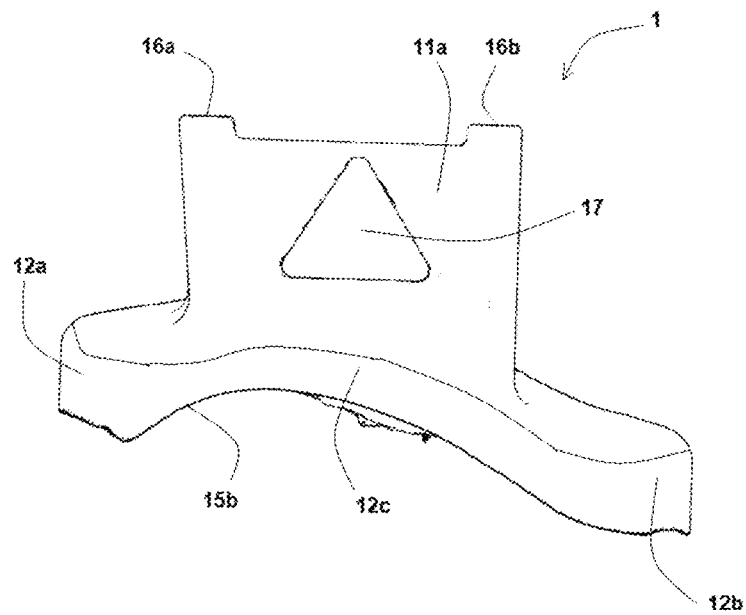
Figure 4D:
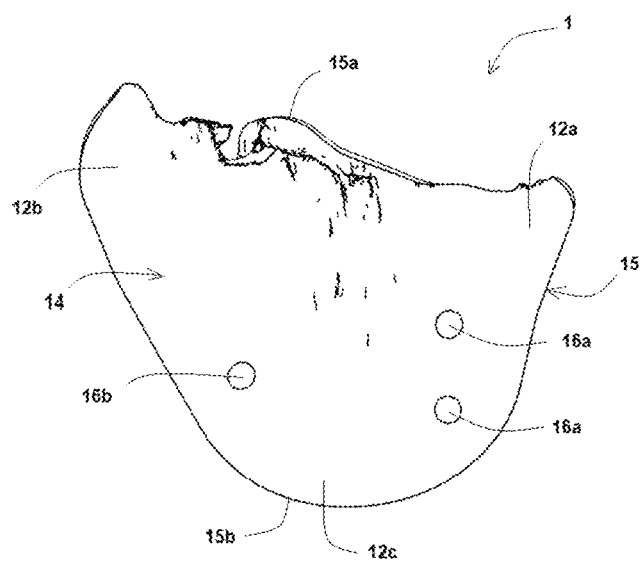

The system according to this invention is characterized in that it comprises a first alignment guide o fixed femoral guide (1). This fixed femoral guide (1), suitable for surgical use and designed from the bone model of the patient's femur, is intended to be placed on the patient's femur and to remain attached to the femur until the preparations for performing femoral cuts are completed, as will be explained later. FIGS. 4A, 4B, 4C and 4D show an embodiment of the fixed femoral guide (1). FIG. 4A shows a perspective of the fixed femoral guide (1) and FIGS. 4B, 4C and 4D show, respectively, a top plan view, a rear view, and a bottom plan view, showing the particular structural features of the fixed femoral guide in detail. In the particular embodiment of figures, the fixed femoral guide (1) comprises a curved lower portion (12) provided with a central part (12c) and two lateral wings or extensions (12a, 12b) that extend from the central part (12c) towards two opposite sides of the fixed femoral guide (1). The central part (12c) comprises a flattened rear part and an anterior part that can have a certain elevation with respect to the rear part. Additionally, this lower portion (12) has an upper face (13) and a lower face (14) opposed to each other and delimited by a contour (15). The fixed femoral guide (1) according to the present invention has the particularity of presenting an essentially concave although with a variable curvature surface, this surface being configured to contact the femur in an adaptive manner when the fixed femoral guide (1) is placed on the femur. More specifically, the fixed femoral guide (1) is placed on the femur, resting substantially on the anterior metaphyseal region of the femur in an area close to the articular surface of the femoral condyles, surrounding said articular surface but not overlapping the articular surface. In the particular embodiment of FIGS. 4A-4D, said curved surface is included in the lower face (14). Additionally, the fixed femoral guide (1) is characterized in that it comprises an irregular edge (15a) configured to be adapted to the area of the femoral condyles surrounding the articular cartilage. In the embodiment of figures, the contour (15) comprises an arched and substantially rectilinear posterior section (15b) and an anterior section defined by the irregular edge (15a). The irregular edge (15a) allows the fixed femoral guide to adapt to the femoral trochlea just at the limit of the articular cartilage but without overlapping or resting on said articular cartilage. Thanks to this geometric configuration, the fixed femoral guide (1) is designed to be placed on a healthy area of the femoral bone. The exact configuration of the irregular edge (15a) and the curved surface of the lower side (14) laying on the femur is variable, calculated in a customized way in the preoperative study to perfectly adapt to the anatomical specific features of the femur of each patient.

Figure 8:
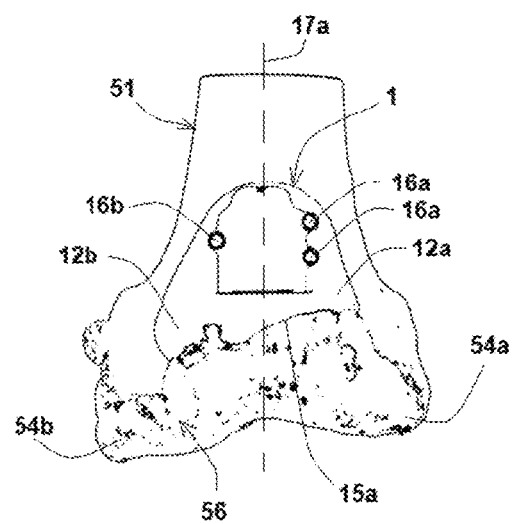
FIGS. 8 to 10 show images of a bone model illustrating the placement and adaptation of the fixed femoral guide on the femur.
Figure 9:
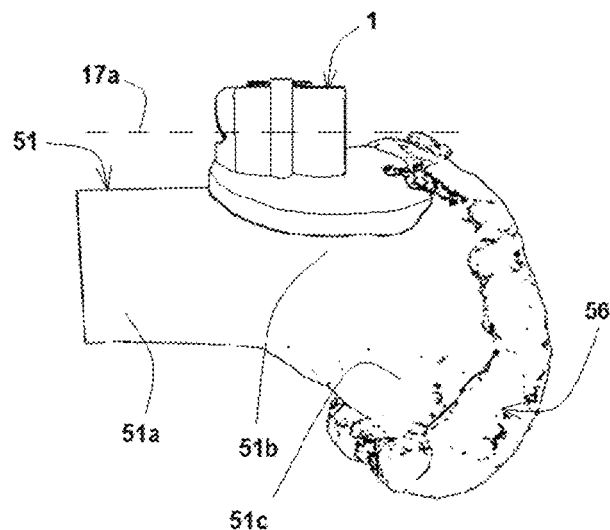
Figure 10:
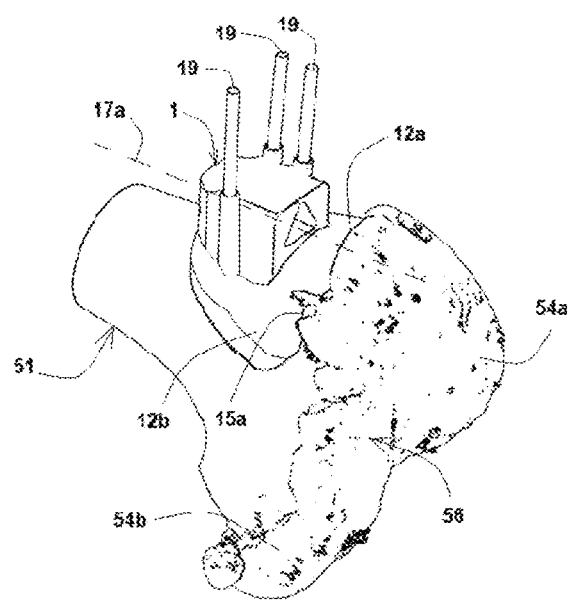

FIGS. 8 to 10 show images of a bone model illustrating the placement and adaptation of the fixed femoral guide (1) of the present embodiment to the bone surface of the femur. It is particularly advantageous that the fixed femoral guide (1) lies substantially on the anterior metaphyseal region of the patient's femur without invading the articular cartilage area. Thus, the fixed femoral guide (1) lays on a healthy part of the bone coupling perfectly and unequivocally in a single position on the patient's bone, unlike other customized conventional alignment systems whose customized components lay on the diseased zone of the joint, with the presence of osteophytes on the deteriorated articular surfaces (62) being common (see FIG. 3). The contact of the alignment components on these deteriorated articular surfaces (62) with defects in the articular cartilage can introduce inaccuracies to be avoided.

FIG. 8 illustrates the placement of the fixed femoral guide (1) on the femur. As shown in figure, the lateral extensions (12a, 12b) are arranged over the metaphyseal region of the femur (51) in areas adjacent to the lateral condyle (54a) and the medial condyle (54b) respectively. Optionally, as clearly shown in FIGS. 4B-4D, a lateral extension (12b) of the fixed femoral guide (1) has a length or dimension greater than the length of the other lateral extension (12a). The longer lateral extension (12b) is placed on the metaphyseal region of the femur in an area adjacent to the most prominent internal medial condyle (54b), optimizing the adaptation of the fixed femoral guide (1) to the femur.

The fixed femoral guide (1) of the present embodiment additionally comprises an upper portion (11). This upper portion (11) is located on the central part (12c) and is attached to the lower portion (12) customized for each patient. Both upper (11) and lower (12) portions form a single piece in the particular embodiment of figures.

The fixed femoral guide (1) is also characterized in that it comprises a fixation element to allow the attachment of the fixed femoral guide (1) to the femur. Optionally, as in the embodiment of FIGS. 4A-4B, the upper portion (11) of the fixed femoral guide (1) comprises a rectangular protrusion (11a) protruding above the lower portion (12) and the fixation element comprises three through holes (16a, 16b) located on opposite sides of the rectangular protrusion (11a). These through holes (16a, 16b) pass through the rectangular protrusion (11a) and the lower portion (12), thus being configured to house or receive pins (19) for fixing the fixed femoral guide (1) to the femur (51), as represented in the bone model of FIG. 10. Optionally, the holes (16a, 16b) have relative angles or directions that can be variable or different, so that this configuration prevents unwanted disconnection of the pins (19) and contributes to reinforce the adaptation of the fixed femoral guide to the femur. Otherwise, the exact number and arrangement of the through holes (16a, 16b) may vary.

The fixed femoral guide (1) additionally comprises a connection element that allows two additional joinable femoral guides (2, 3) to be separately and consecutively coupled. Optionally, as in the embodiment of figures, the connection element of the fixed femoral guide (1) comprises a through hole (17) as a rail. This through hole (17) extends substantially in the direction of a longitudinal axis (17a) through the rectangular protrusion (11a) of the upper portion (11). As will be explained later when the configuration of the joinable femoral guides (2, 3) is detailed, it is particularly advantageous that the direction of the longitudinal axis (17a) of the through hole (17) is parallel to the mechanical axis of the femur (in anterior view of the femur) and parallel to the diaphyseal axis of the femur (in lateral view of the femur) when the fixed femoral guide (1) is placed on the femur.

Once fixed to the femur, the fixed femoral guide (1) is held in this position until the preparations for the femoral cuts are completed, as will be detailed below and as illustrated in FIGS. 11 to 19.

Figure 11:
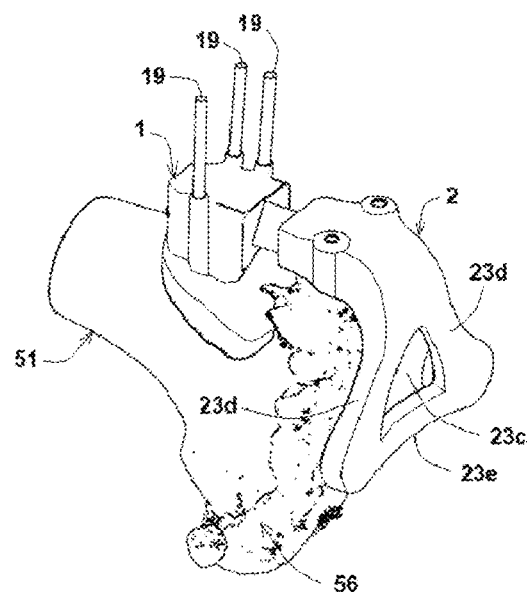
FIGS. 11 to 13 show images of a bone model illustrating the coupling between the fixed femoral guide and the first joinable femoral guide.
Figure 12:
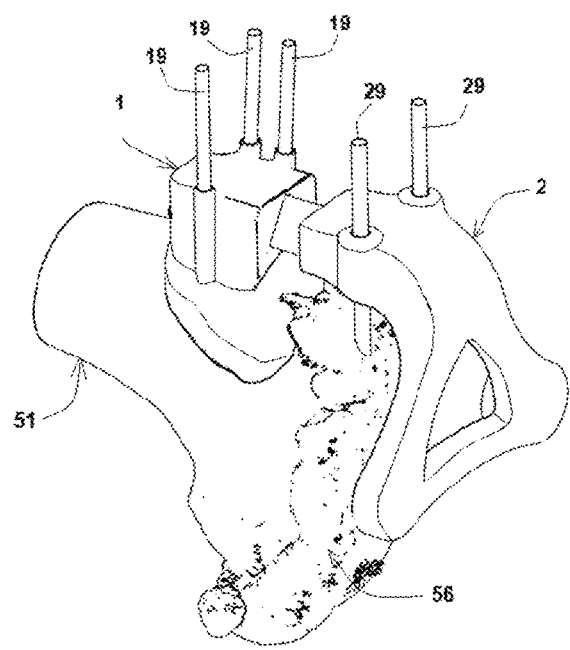
Figure 13:
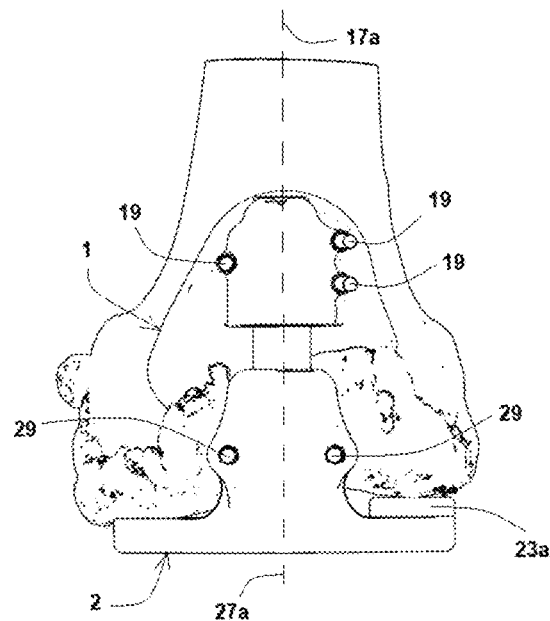

The alignment system of the invention comprises a first joinable femoral guide (2) that can be coupled to the fixed femoral guide (1). FIGS. 5A, 5B, 5C and 5D illustrate a particular embodiment of this first joinable femoral guide (2) and FIGS. 11 to 13 show representations of a bone model that illustrate the coupling between the fixed femoral guide (1) of FIGS. 4A-4D and the first joinable femoral guide (2) of FIGS. 5A-5D. In this specific example, for this connection or coupling to be made between both guides (1, 2), the first joinable femoral guide (2) comprises a posterior portion (21) provided with a connection element that is complementary to the connection element of the fixed femoral guide (1). To do this, the complementary connection element has a geometric configuration adapted to the shape and dimension of the connection element of the fixed femoral guide (1). Optionally, as in the embodiment of the figures, the complementary connection element is an elongated rail (27) configured to be movably or slidably coupled to the through hole (17) of the fixed femoral guide (1). To this end, the rail (27) also extends substantially along a longitudinal axis (27a) and its shape and dimension are adjusted to the shape and dimension of the through hole (17) of the fixed femoral guide (1). This way, both guides (1, 2) are simply coupled by means of a relative sliding movement between both connection components (17, 27) in the direction of the axes (17a, 27a), these axes (17a, 27a) remaining superimposed as can be seen in FIG. 13. Thus, when the fixed femoral guide (1) and the first joinable femoral guide (2) are connected, the rail (27) longitudinally passes through the through hole (17) allowing the separable coupling between the guides (1, 2) in a simple way.

Figure 5A:
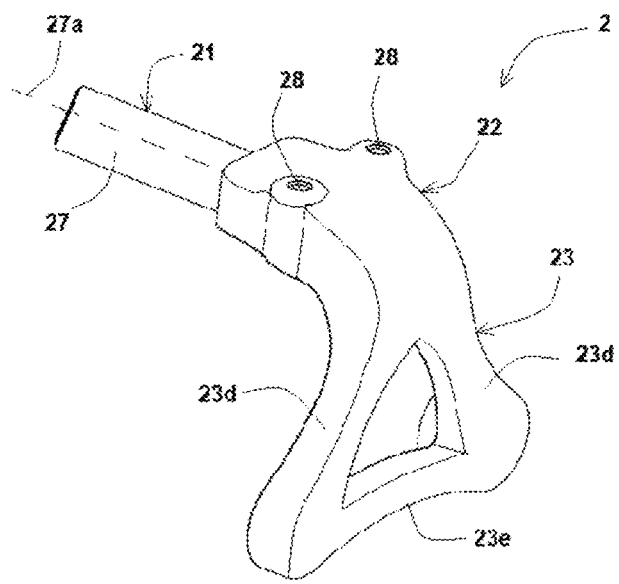
FIGS. 5A, 5B, 5C, and 5D show respectively two perspectives, a side view and a plan view of an embodiment of the first joinable femoral guide that can be coupled to the fixed femoral guide of FIGS. 4A-4D.
Figure 5B:
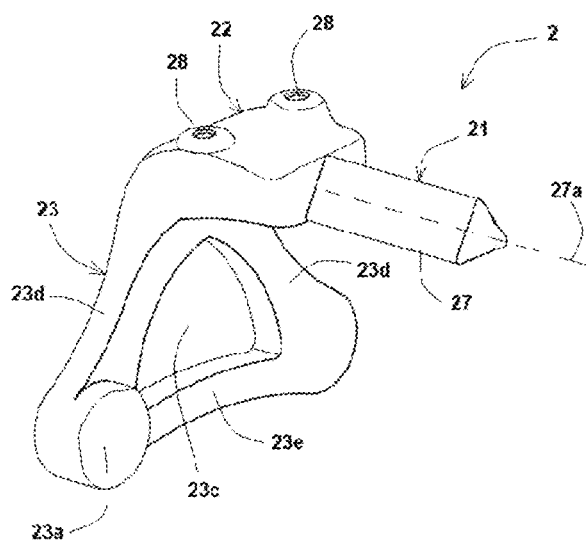
Figure 5C:
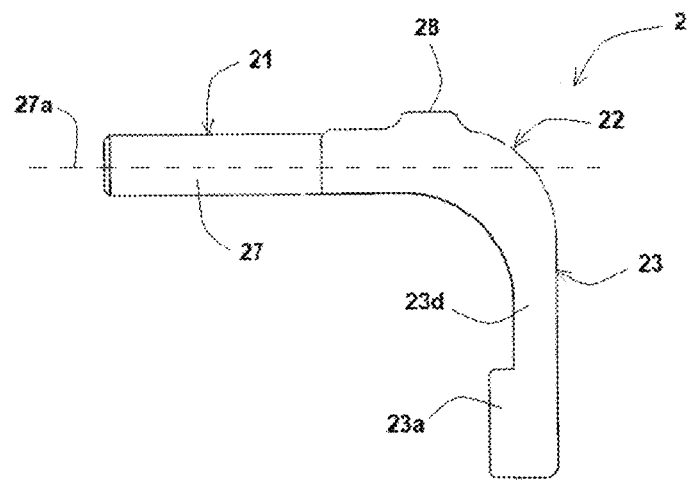
Figure 5D:
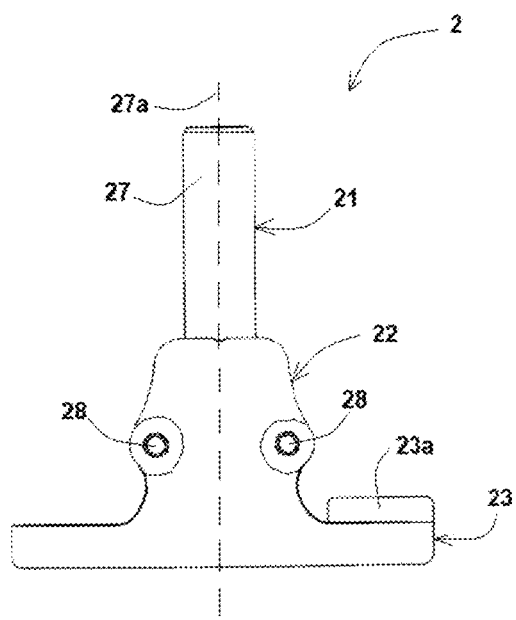

As can also be seen in FIGS. 5A, 5B and 5D, the first joinable femoral guide (2) of the illustrated embodiment further comprises an intermediate portion (22), widened in relation to the posterior portion (21), and an anterior portion (23) extending from the intermediate portion (22) in a direction that forms a certain angle with the axis (27a) of the rail (27). Optionally, as in the described embodiment, the anterior portion (23) comprises two tilted arms (23d) that are substantially vertical and a substantially horizontal arm (23e), with these arms (23d, 23e) presenting a triangular arrangement. As can be clearly seen in FIGS. 5B and 11, the arms (23d, 23e) define a central cavity (23c), with the first joinable femoral guide (2) also presenting a projection (23a) in one of the lower apexes of the triangular arrangement formed by the arms (23d, 23e). Thanks to these structural members, it is possible to easily limit the displacement of the first joinable femoral guide (2) in relation to the fixed femoral guide (1). For this purpose, as shown in FIGS. 11-13, once the fixed femoral guide (1) is properly positioned on the femur (51), the through hole (17) of the first joinable femoral guide (2) can slide inside the rail (27) of the fixed femoral guide (1) until the anterior portion (23) of the first joinable femoral guide (2) contacts both femoral condyles (54). The projection (23a) facilitates the contact of the first joinable femoral guide (2) on both condyles (54a, 54b), as can be especially seen in FIG. 13, improving the stability of the coupling between both guides (1, 2).

The function of the central cavity (23c) is to provide a window for a better visualization during the surgical procedure, additionally allowing the introduction of instruments, for example with the purpose of carrying out checks that may be necessary during surgery.

Figure 14:
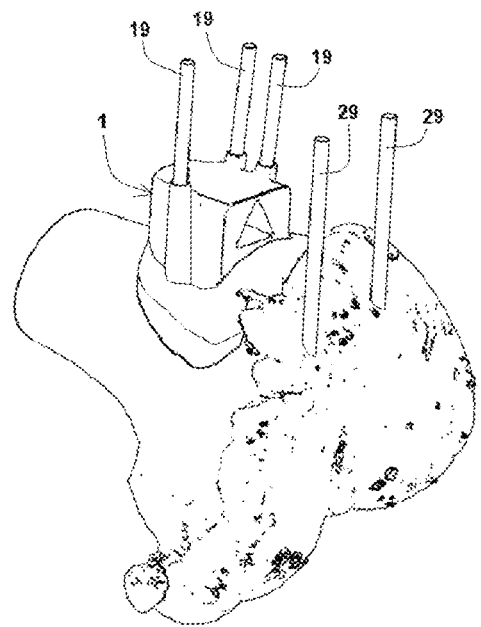
FIGS. 14 to 17 illustrate the functionality of the fixed femoral guide to allow the distal cut of the femur to be made.
Figure 15:
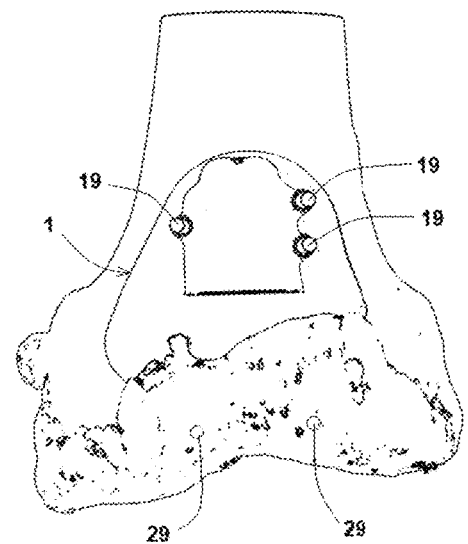
Figure 16:
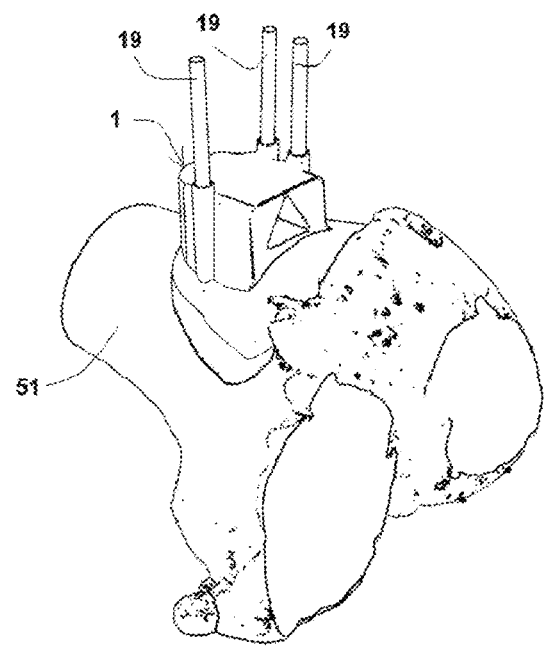
Figure 17:
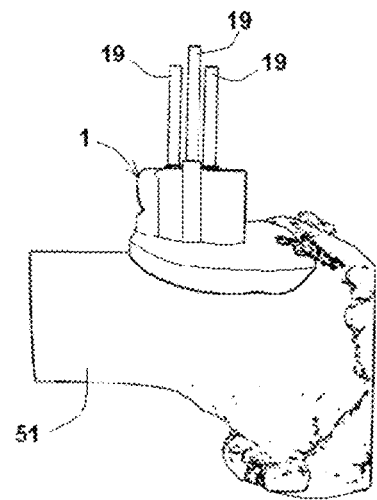

The intermediate portion (22) of the first joinable femoral guide (2) has the additional particularity of being provided with an alignment member. In the embodiment of the figures, the alignment member comprises a pair of indicators or through holes (28) that are substantially parallel and pass through the intermediate portion (22). The function of these holes (28) is to allow drilling to be made in the anterior cortex of the femur, once the fixed femoral guide (1) is placed on the femur and the guides (1, 2) are coupled. The perforations made allow the insertion of metallic pins (29) in the femur through these holes (28), with these metallic pins (29) being of the type commonly used for the placement of a distal cutting guide of a conventional TKP. In the alignment system of the invention, the configuration of the holes (28) is calculated and planned in a customized way from the preoperative study. Thus, the position of the holes (28) is precisely determined so that the conventional distal cutting guide can be mounted on the pins (29) presenting an orientation that enables a distal cut to be made perpendicular to the mechanical axis of the femur. For this purpose, once the metal pins (29) have been placed through the holes (28), the first joinable femoral guide (2) is removed, leaving the pins (29) positioned as shown in FIGS. 14 and 15. The first joinable femoral guide (2) can be removed by cutting the rail (27) with a chisel. Subsequently, a conventional distal cutting guide can be placed on the pins (29) to make a distal cut perpendicular to the mechanical axis of the femur (cut illustrated in FIGS. 16 and 17).

Preferably, the direction of the axis (27a) of the rail (27) is parallel to the mechanical axis of the femur (in anterior view) and parallel to the diaphyseal axis of the femur (in lateral view), the angle between the rail (27) and the anterior portion (23) is substantially straight (as in the embodiment of figures) and the plane defined by the holes (28) is perpendicular to the mechanical axis of the femur, when the fixed femoral guide (1) is placed on the femur and the first joinable guide (2) is coupled to the fixed femoral guide (1). This way, the plane defined by the holes (28) is parallel to the distal cut, made using the conventional distal cut guide placed on the pins (29).

Thanks to the coupling between the guides (1, 2) and the customized and precise coupling of the fixed femoral guide (1) on the healthy bone surface of the patient, the alignment system according to the invention allows to precisely transfer the preoperative calculations to the surgical procedure carried out on the patient.

Figure 18:
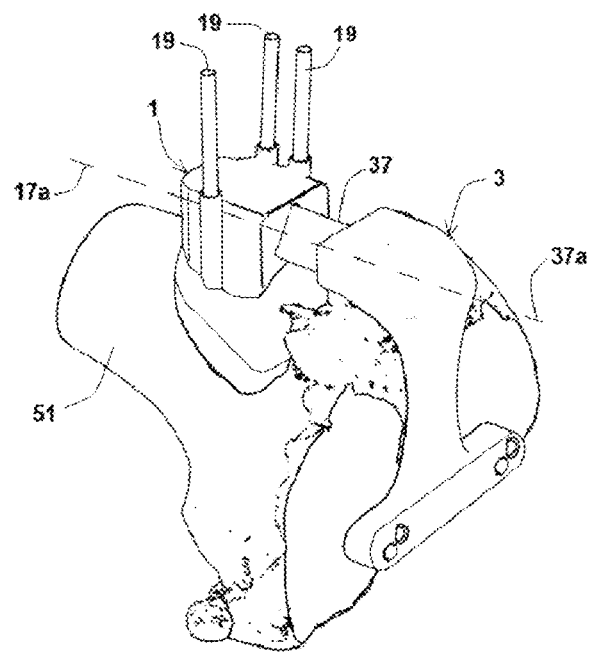
FIGS. 18 and 19 show images of a bone model illustrating the coupling between the fixed femoral guide and the second joinable femoral guide, as well as the functionality of this second joinable femoral guide.
Figure 19:
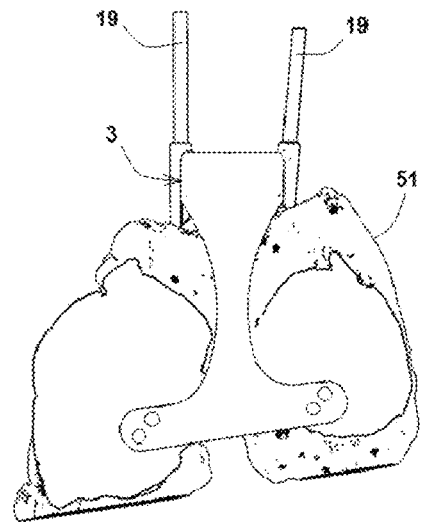

The alignment system of the invention comprises a second joinable femoral guide (3) that can be coupled to the fixed femoral guide (1). FIGS. 6A, 6B, 6C, and 6D illustrate a particular embodiment of this second joinable femoral guide (3). FIGS. 18 and 19 illustrate the coupling between the second joinable femoral guide (3) of FIGS. 6A-6D and the fixed femoral guide (1) of FIGS. 4A-4D. In this particular example, to perform the coupling between both guides (1, 3), the second joinable femoral guide (3) comprises a posterior portion (31) provided with a complementary connection element in relation to the connection element of the femoral guide fixed (1). This supplementary connection element has a geometric configuration adapted to the shape and dimension of the connection element of the fixed femoral guide (1). Optionally, the complementary connection element is an elongated rail (37), similar to that of the first joinable femoral guide (2), configured to be movably or slidably coupled in relation to the through hole (17) of the fixed femoral guide (1). To this end, the rail (37) extends along a longitudinal axis (37a) and its shape and dimension are adjusted to the shape and dimension of the through hole (17) of the fixed femoral guide (1). This way, the fixed femoral guide (1) and the second joinable femoral guide (3) can be easily coupled, by means of a relative displacement in the direction of the axes (17a, 37a) which remaining superimposed as shown in FIG. 18. Thus, when the fixed femoral guide (1) and the second joinable femoral guide (3) are coupled, the rail (37) longitudinally passes through the through hole (17) of the fixed femoral guide (1). The displacement is limited by the contact of the second joinable femoral guide (3) with the distal femoral surface previously cut.

The second joinable femoral guide (3) also optionally comprises an intermediate portion (32), widened in relation to the posterior portion (31), slightly curved, and connected with an anterior portion (33). The anterior portion (33) extends from the intermediate portion (32) in a direction that forms a certain angle with the posterior portion (31). Optionally, as in the embodiment of figures, the anterior portion (33) comprises an arm (33d) substantially vertical and an arm (33e) tilted in relation to the arm (33d), approximately presenting these arms (33d, 33e) an inverted T-shaped configuration.

Figure 6A:
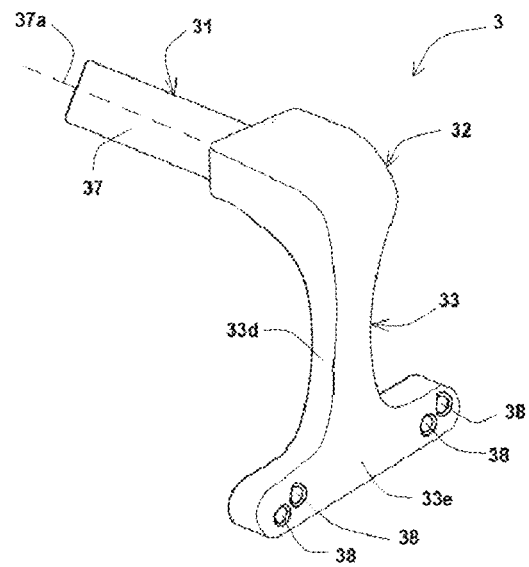
FIGS. 6A, 6B, 6C, and 6D show respectively two perspectives, a front view and a lateral view of an embodiment of the second joinable femoral guide that can be coupled to the fixed femoral guide of FIGS. 4A-4D.
Figure 6B:
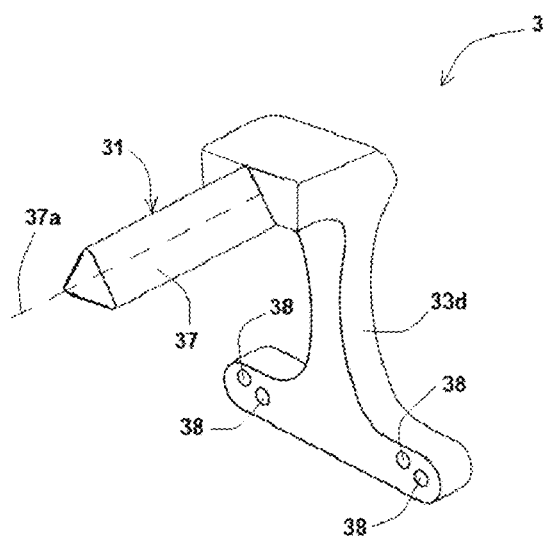
Figure 6C:
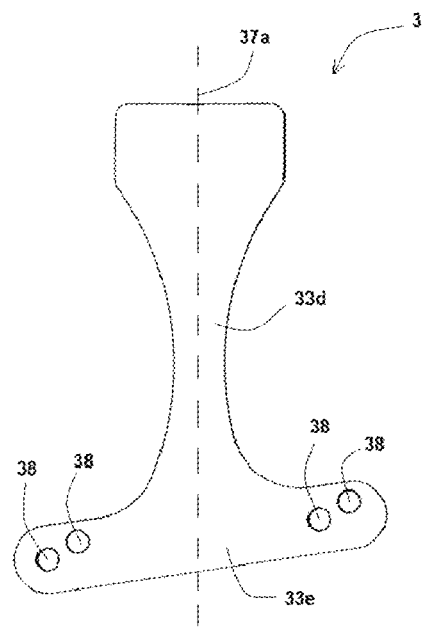
Figure 6D:
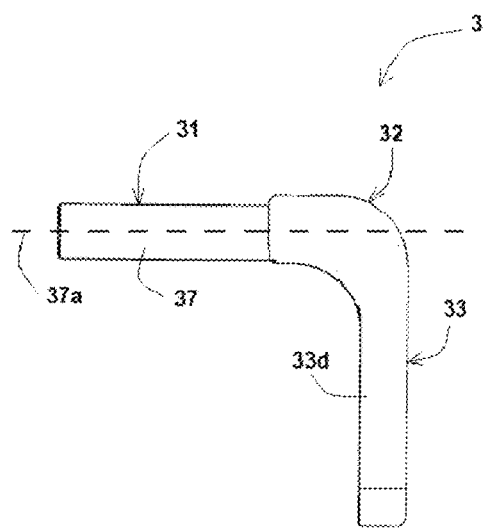

The second joinable femoral guide (3) has the particularity of comprising an alignment member. The function of this alignment member is to allow drilling of the femur, once the distal cut has been made, suitable for the subsequent placement of a 4-in-1 cutting guide of a conventional TKP. Preferably, the alignment member comprises a plurality of pairs of indicators or through holes (38) that are parallel, each pair being arranged in an aligned manner in the tilted arm (33e) of the anterior portion (33). As can be seen in FIG. 6C, in this particular embodiment, the second joinable femoral guide (3) has two pairs of holes (38). In the alignment system of the invention, the configuration of the holes (38) is calculated and planned in a customized way from the preoperative study. The pairs of holes (38) have the particularity of being aligned parallel to the epicondylar line, when the fixed femoral guide (1) is placed on the femur and the second joinable femoral guide (3) is coupled to the fixed femoral guide (1). This alignment feature provides proper rotation for the femoral prosthetic component.

In the embodiment of figures, the position of the through holes (38) is calculated by means of a preoperative CAT. Its geometry allows drilling to be carried out, for the subsequent placement of a conventional 4-in-1 guide for making the anterior, anterior oblique, posterior and posterior oblique femoral cuts. The size of the femoral prosthetic component to be used is also calculated preoperatively, which will define the conventional cutting guide suitable for that size. The joinable femoral guide (3) is removed after drilling, as well as the fixed femoral guide (1).

Preferably, the direction of the axis (33a) of the rail (37) is parallel to the mechanical axis of the femur (in anterior view) and parallel to the diaphyseal axis of the femur (in lateral view) and the angle between the rail (37) and the anterior portion (33) is substantially straight (as in the embodiment of the figures), when the fixed femoral guide (1) is placed on the femur and the second joinable guide (3) is coupled to the fixed femoral guide (1) resting on the femur once the distal cut has been made.

Thanks to the separable coupling between the guides (1, 3) and the customized and precise coupling of the fixed femoral guide (1) on the healthy bone surface of the patient, the alignment system according to the invention allows to transfer with great precision the preoperative calculations to the surgical procedure carried out on the patient. After completing the femoral cuts, the femur is prepared for the placement of the femoral prosthesis.

As previously explained, the fixed femoral guide (1) and the joinable femoral guides (2, 3) are not cutting guides but auxiliary alignment members for the precise drilling of the femur, compatible with the subsequent placement of conventional cutting guides commonly used to perform the distal cut and the other femoral cuts in a TKA.

Figure 7A:
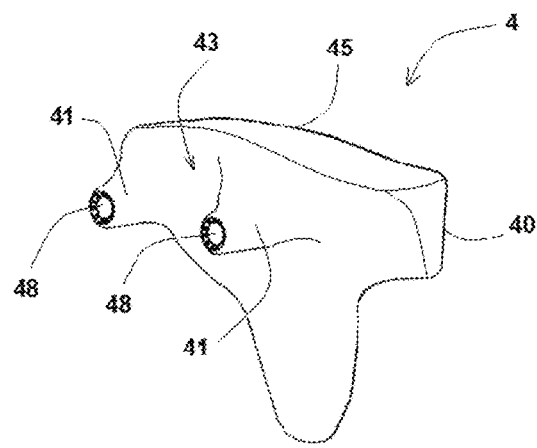
FIGS. 7A, 7B, and 7C show respectively a front perspective, a front view and a rear perspective of an embodiment of the tibial guide of the alignment system of the invention.
Figure 7B:
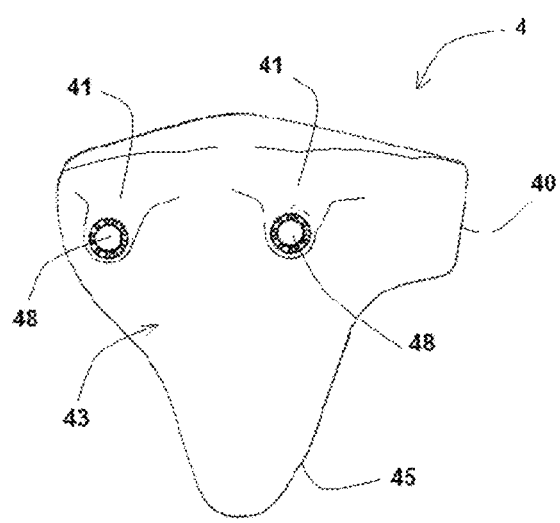
Figure 7C:
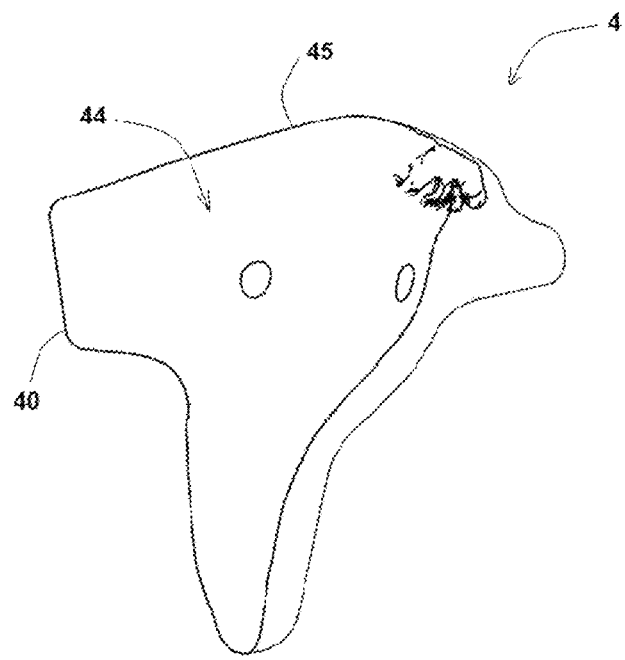

The alignment system of the invention is completed with a fourth tibial guide (4). Similar to the fixed femoral guidewire (1), the tibial guide (4) is calculated from a bone model of the patients tibia, obtained using a CT scan or other diagnostic method with equivalent performance. FIGS. 7A, 7B, and 7C show an embodiment of the tibial guide (4). The images of the bone model in FIGS. 20 to 24 illustrate the placement and functionality of the tibial guide (4). This fourth tibial guide (4) is specifically designed to be placed and adapted over an anteromedial region of the tibia, reaching an area adjacent to the articular surface but not overlapping said articular surface. This way, the tibial guide (4) lays precisely and unequivocally on the healthy surface of the patient's bone, outside the diseased articular surface, obtaining greater surgical precision in relation to other conventional techniques.

Figure 20:
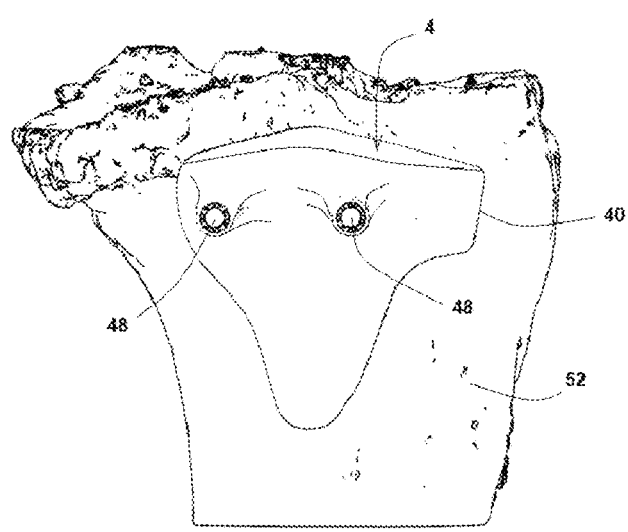
FIGS. 20 to 22 show images of a bone model that illustrate the placement and adaptation of the tibial guide on the tibia.
Figure 21:
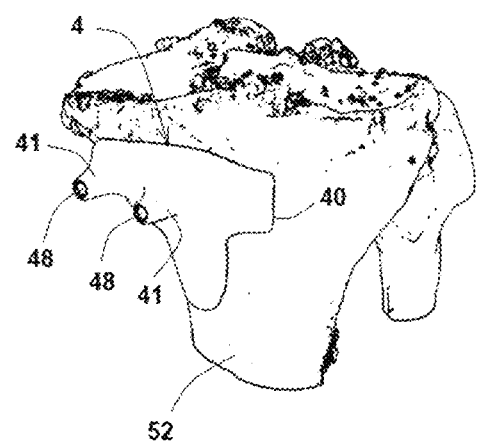
Figure 22:
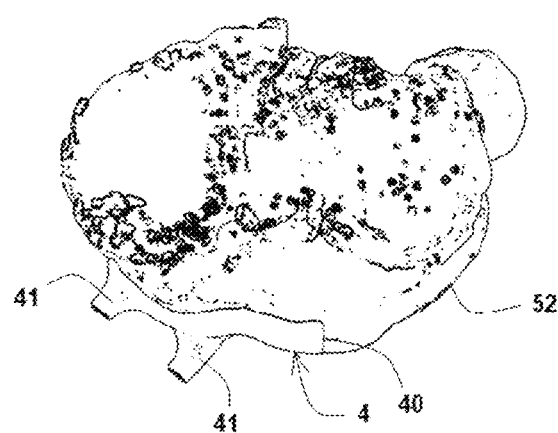
Figure 23:
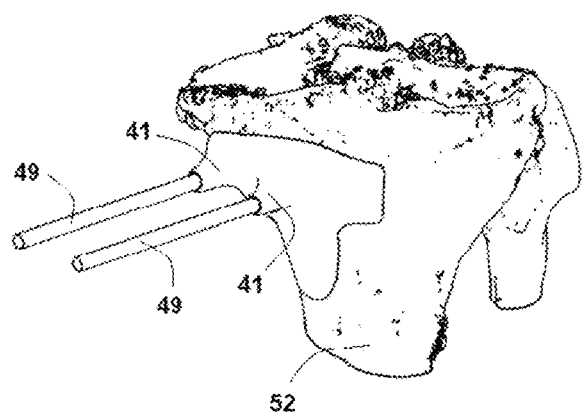
FIGS. 23 and 24 illustrate the functionality of the tibial guide to allow the tibial cut to be made.
Figure 24:
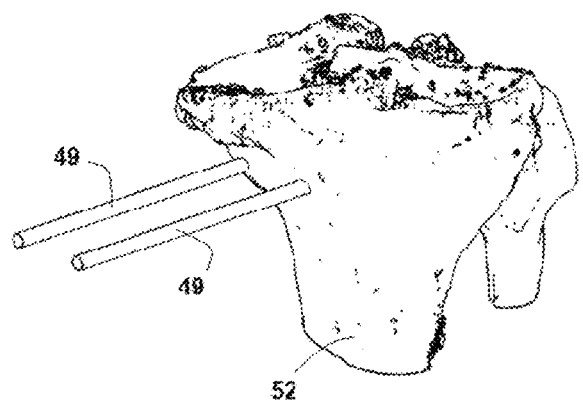

Optionally, as in the embodiment of figures, the tibial guide (4) has an anterior face (43) and a posterior face (44) opposed to each other and delimited by a contour (45). The tibial guide (4) of the invention has the particularity of presenting a surface of variable curvature, comprised in the posterior face (44) and designed to adapt to the healthy part of the tibia without invading the articular cartilage. To this end, an upper section of the contour (45) is placed bordering the articular cartilage of the tibia, as can be seen in FIGS. 20 to 22. The tibial guide (4) is further characterized in that it comprises an alignment member, also customized. In the described embodiment, the alignment member comprises a pair of indicators or through holes (48) that go through two protrusions (41) of the tibial guide (4). The function of these holes (48) is to allow the perforation of the tibia for the placement of metallic pins (49) as illustrated in FIG. 23. These pins (49) are compatible with the tibial cutting guide of a conventional TKP. Preferably, the plane defined by the protrusions (41) of the tibial guide (4) and the direction of the through holes (48) are perpendicular to the mechanical axis of the tibia (in frontal view), to allow a tibial cut to be made parallel to the direction of the pins (49) and perpendicular to the tibial mechanical axis. Once the pins (49) are placed, the alignment tibial guide (4) of the invention is removed as illustrated in FIG. 24. Over these pins (49) the conventional tibial cutting guide (not shown) can be placed later to carry out the tibial cut.

Additionally, the contour (45) comprises a side edge (40), calculated by means of the preoperative CAT, to allow for the making of a mark during surgery for the indication of the limit of rotation of the tibial prosthetic component.

The guides (1, 2, 3 4) of the described embodiment are manufactured by additive manufacturing (3D printing) of a thermoplastic material, a method that allows the sustainable manufacturing of components at tightened costs. However, other manufacturing alternatives compatible with the essence of the invention are admissible.

The invention claimed is:

1. An extramedullary alignment system of instruments used in total knee arthroplasty, comprising:
   a fixed femoral guide configured to be placed on a femur of a patient, comprising a curved surface partially delimited by an irregular edge and configured to fit and tightly contact the femur, surrounding an articular surface of the femoral condyles without overlapping said articular surface, a fixation element for the joint of the fixed femoral guide to the femur, and a connection element,
   two joinable femoral guides detachably and consecutively coupled to the fixed femoral guide through the connection element of the fixed femoral guide; and
   a tibial guide configured to be placed on an anteromedial region of a patient's tibia, comprising a curved surface configured to adapt to the tibia, surrounding the articular surface of the tibia without overlapping said articular surface.

2. The alignment system, according to claim 1, wherein the curved surface and the irregular edge of the fixed femoral guide are designed from a bone model obtained by a CAT scan.

3. The alignment system, according to claim 1, wherein the fixation element of the fixed femoral guide comprises a plurality of through holes with different relative angulation.

4. The alignment system, according to claim 1, wherein the fixed femoral guide comprises a curved lower portion provided with a central part and two lateral extensions extending from the central part towards two opposite sides of the fixed femoral guide, wherein the lower portion has an upper face and a lower face separated by a contour, being the curved surface adaptable to the femur comprised in the lower face and being the irregular edge comprised in an anterior section of the contour.

5. The alignment system, according to claim 4, wherein one of the two lateral extensions of the fixed femoral guide has a greater length than a second one of the two lateral extensions for a better adaptation of the fixed femoral guide to the femur.

6. The alignment system, according to claim 4, wherein the fixed femoral guide comprises an upper portion located on the central part and provided with a protrusion, wherein the fixation element of the fixed femoral guide comprises three through holes located on opposite sides of the protrusion passing through the protrusion and the lower portion, and wherein two of the holes have an angulation different to the angulation of the third hole.

7. The alignment system, according to claim 6, wherein the upper portion and the lower portion form a single piece.

8. The alignment system, according to claim 1, wherein the connection element of the fixed femoral guide comprises a through hole that extends substantially in the direction of a longitudinal axis passing through a protrusion protruding above the curved surface.

9. The alignment system, according to claim 8, wherein the longitudinal axis of the through hole has an arrangement parallel to a mechanical axis of the femur when the fixed femoral guide is placed on the femur.

10. The alignment system, according to claim 1, wherein a first one of the two joinable femoral guides comprises two through holes, the holes being arranged in a plane perpendicular to a mechanical axis of the femur when the fixed femoral guide is placed on the femur and the first one of the two joinable femoral guide is coupled to the fixed femoral guide.

11. The alignment system, according to claim 10, wherein the configuration of the through holes is calculated from a bone model obtained by a CAT scan.

12. The alignment system, according to claim 10, wherein the first one of the two joinable femoral guides comprises a posterior portion, comprising a supplementary connection element having a geometric configuration adapted to the shape and dimension of the connection element of the fixed femoral guide, an intermediate portion widened in relation to the posterior portion that houses the through holes, and an anterior portion that extends from the intermediate portion in a direction that forms a substantially right angle with the posterior portion.

13. The alignment system, according to claim 12, wherein the supplementary connection element is an elongated rail extending in the direction of a longitudinal axis, presenting a shape and dimension adjusted to the shape and dimension of a through hole of the fixed femoral guide and being movable in relation to said through hole, so that the fixed femoral guide and the first one of the two joinable femoral guides are configured to be coupled by a sliding relative movement in the direction of the axis.

14. The alignment system, according to claim 12, wherein the anterior portion has a triangular arrangement, comprising a projection at one of a plurality of apexes of the triangular arrangement to facilitate the contact of the anterior portion on both femoral condyles when the fixed femoral guide is placed on the femur and the first one of the two joinable femoral guides is coupled to the fixed femoral guide.

15. The alignment system, according to claim 14, wherein the anterior portion comprises two tilted arms that are substantially vertical and a third substantially horizontal arm, making up the triangular arrangement and delimiting a central cavity.

16. The alignment system, according to claim 10, wherein the position of the through holes is calculated from a bone model obtained by CAT scan.

17. The alignment system, according to claim 1, wherein a second one of the two joinable femoral guides comprises at least a pair of through holes, being these holes aligned parallel to an epicondylar line of the femur when the fixed femoral guide is placed on the femur and the second joinable femoral guide is coupled to the fixed femoral guide.

18. The alignment system, according to claim 16, wherein the second one of the two joinable femoral guides comprises a posterior portion, provided with a supplementary connection element that has a geometric configuration adapted to the shape and dimension of the connection element of the fixed femoral guide and an anterior portion that forms a substantially right angle with the posterior portion and that houses the holes.

19. The alignment system, according to claim 18, wherein the supplementary connection element is an elongated rail extending in the direction of a longitudinal axis, presenting a shape and dimension adjusted to the shape and dimension of a through hole of the fixed femoral guide and being movable in relation to said through hole, so that the fixed femoral guide and the second one of the two joinable femoral guides are configured to be coupled by a sliding relative movement in the direction of the axis.

20. The alignment system, according to claim 18, wherein the anterior portion comprises a vertical arm and a second tilted arm crossed by the pair holes.

21. The alignment system, according to claim 1, wherein the tibial guide is designed from a bone model obtained by a CAT scan.

22. The alignment system, according to claim 1, wherein the tibial guide comprises two through holes arranged in a plane perpendicular to a tibial mechanic axis when the tibial guide is placed on the tibia.

* * * * *